(12) United States Patent
Godett et al.

(10) Patent No.: US 8,146,853 B2
(45) Date of Patent: Apr. 3, 2012

(54) OPTICAL LASER FIBER REEL

(75) Inventors: Jeanne Godett, Granite Bay, CA (US); Aric Sven, Antioch, IL (US)

(73) Assignee: Jeanne Godett, Scottsdale, AZ (US)

(*) Notice: Subject to any disclaimer, the term of this patent is extended or adjusted under 35 U.S.C. 154(b) by 268 days.

(21) Appl. No.: 12/568,587

(22) Filed: Sep. 28, 2009

(65) Prior Publication Data

US 2011/0073700 A1    Mar. 31, 2011

(51) Int. Cl.
*B65H 75/38*    (2006.01)
(52) U.S. Cl. .................. 242/388.1; 242/388.5; 242/398; 242/406
(58) Field of Classification Search .................. 242/406, 242/407, 398, 388.1, 388.5, 378.1
See application file for complete search history.

(56) References Cited

U.S. PATENT DOCUMENTS

| | | | | |
|---|---|---|---|---|
| 4,901,938 A * | 2/1990 | Cantley et al. | ............. | 242/378.1 |
| 5,490,805 A * | 2/1996 | Bredesen | ........................ | 441/75 |
| 5,853,136 A * | 12/1998 | Lai | ............................ | 242/388.1 |
| 6,015,110 A * | 1/2000 | Lai | ............................ | 242/388.1 |
| 7,229,042 B2 * | 6/2007 | Thebault et al. | ........... | 242/388.1 |
| 7,367,522 B2 * | 5/2008 | Chen | ........................... | 242/378.1 |
| 7,992,259 B2 * | 8/2011 | Goldstein et al. | ................ | 24/18 |

* cited by examiner

*Primary Examiner* — Sang Kim
(74) *Attorney, Agent, or Firm* — Stetina Brunda Garred & Brucker

(57) ABSTRACT

A universal laser fiber reel for use with an optical laser fiber, having a base with a base plate, the base plate having a base hub and base wall with the base wall having a base wall width not less than a minimum laser fiber wind length. A fiber cage proximate the base wall radially stores the laser fiber in the reel, the fiber cage having a fiber cage radius equal to a minimum laser fiber bend radius and a fiber cage width not less than the minimum laser fiber wind length of the laser fiber.

11 Claims, 5 Drawing Sheets

OPTICAL LASER FIBER REEL

CROSS-REFERENCE TO RELATED APPLICATIONS

Not Applicable

STATEMENT RE: FEDERALLY SPONSORED RESEARCH/DEVELOPMENT

Not Applicable

BACKGROUND

The present invention relates generally to a universal laser fiber reel for use with an optical laser fiber.

Lasers are used in a variety of fields, including medicine and dentistry. Lasers are used for example in surgical procedures to remove tissue and in cosmetic dentistry to whiten teeth. An optical laser fiber is used to deliver the laser energy from the laser device to the surgical site or targeted tooth.

The housing in which the optical laser fiber is stored for later use in surgical and dental procedures should provide for ready accessibility to the laser fiber and also be able to withstand the sterilization process of the laser fiber. The housing should also be able to store the laser fiber in a manner that does not excessively twist, coil, or bend the laser fiber. Otherwise, the laser fiber may be damaged, thereby affecting the transmission of laser energy from the laser to the target site.

It is understood that prior art optical fiber housing systems, including the Ivoclar-Odyssey, store the optical fiber in a manner that causes the fiber to "backup" and twist around itself. The Ivoclar-Odyssey is a motorized device that appears to attempt to wind the laser fiber around a conical element. However, the housing configuration of the Ivoclar-Odyssey is understood to cause the laser fiber to "bunch up" in the cylinder, resulting in the inconsistent and unpredictable retraction of the laser fiber. The Ivoclar-Odyssey also does not appear to account for the minimum bend radius below which the laser fiber should not be bent, thereby causing the laser fiber to potentially brake or otherwise be damaged. Furthermore, it is understood that the exterior of the Ivoclar-Odyssey is made of a plastic material that cannot be subjected to the searing heat of an autoclave that may be used to sterilize the laser fiber. As a result, the laser fiber from the Ivoclar-Odyssey cannot be sterilized. If the laser fiber is not sterilized, the patients may be exposed to a variety of potentially dangerous pathogens, particularly if parts of the laser fiber have touched the floor or have come into contact with other patients.

Accordingly, there appears to be a need in the art for a new optical laser fiber housing that enables ready retrieval of the optical fiber from storage, can withstand the high temperatures of the sterilization process, and that does not bend the laser fiber below its minimum bend radius.

BRIEF SUMMARY

According to an aspect of the present invention, there is provided a universal laser fiber reel for use with an optical laser fiber. The laser fiber reel comprises a generally cylindrical base having a base plate. The base plate may have a base plate outer surface and a base plate inner surface. The base plate may further have a base hub defining a base hub axis. The base may further have a cylindrical base wall generally orthogonal to the base plate and concentric to the base hub. The base wall may have a base wall outer surface and a base wall inner surface. The base wall inner surface may have a spacer. The base wall may further have a base wall width greater than a minimum laser fiber wind length. The laser fiber reel may further include a generally cylindrical wheel defining a wheel axis concentric to the base hub. The wheel may have a wheel outer surface and an opposing wheel inner surface facing the base plate inner surface. The wheel may be rotateably engageable with the base. The laser fiber reel may further have a fiber cage proximate to the base wall inner surface and concentric to the base hub operative to radially store the laser fiber in the reel. The fiber cage may be a spool. The fiber cage may have a fiber cage radius as measured from the base hub greater than or equal to a minimum laser fiber bend radius. The fiber cage may further have a fiber cage width not less than the minimum laser fiber wind length. The fiber cage may be a plurality of six evenly spaced wheel posts. Each wheel post may have a wheel post first end mounted to the wheel inner surface and a wheel post second end extending from the wheel inner surface toward the base plate inner surface proximate to the base wall inner surface. Each wheel post second end may be rotateably engageable with a spacer mounted to the base wall inner surface. Furthermore, each wheel post second end may have a generally rounded spacer knob sized and configured to be rotateably engageable with the spacer. The laser fiber reel may further have a laser fiber input port on the base plate outer surface operative to receive the laser fiber into the reel.

The laser fiber reel is innovative in that it uniquely enables optical laser fibers of varying sizes to be uniformly housed such that the fiber is not bent below its minimum bend radius. The configuration of the fiber cage enables the laser fiber to be wound in a manner that mitigates the "bunching" or "backing up" of the fiber. The fiber cage width also uniquely enables the laser fiber to be wound around the fiber cage such that the laser fiber does not wind around itself, thereby further mitigating the likelihood of possible damage or breakage of the laser fiber due to bending or coiling below the minimum laser fiber bend radius. Also, its compact configuration enables the laser fiber reel to be readily stored or transported from one procedure site to the next. The laser fiber reel is further innovative in that the laser fiber may continue to be housed in the fiber reel during the process of sterilization. It is foreseeable that the laser fiber will be exposed to various pathogens during the medical and dental procedures for which it is used. Typically, the end of the fiber that is used at the surgical or dental site is cut off upon completion of the procedure and then sterilized in an autoclave. The laser fiber reel enables the medical or dental technician to remove that portion of the laser fiber exposed to the target site, retract the remaining laser fiber onto the fiber cage in the fiber reel and then place the wound laser fiber reel into an autoclave for sterilization. This configuration obviates the need to remove the laser fiber from the laser fiber reel, thereby making the housing and sterilization of the laser fiber onto the laser fiber reel more efficient.

In an embodiment of the present invention, the fiber cage may be mountable to the base plate. In another embodiment, the fiber cage may be mountable to the wheel.

In yet a further embodiment, the laser fiber reel may further include a laser fiber output aperture on the base wall operative to enable the release or retraction of the laser fiber.

In another embodiment, the fiber reel may be made of metal.

According to another embodiment of the present invention, the laser fiber reel further includes a mounting post on the base plate outer surface operative to mount the laser fiber reel to a mounting clip.

In another embodiment, the laser fiber reel may further include a plurality of grip channels on the wheel outer surface.

According to other embodiments of the present invention, the fiber cage may have a fiber cage radius that may be sized and configured for a laser fiber between 200 and 400 micrometers. In another embodiment, the radius of the fiber cage radius may be sized and configured for a laser fiber greater than or equal to 400 micrometers. In yet a further embodiment, the fiber cage radius may be sized and configured for a laser fiber less than or equal to 200 micrometers.

In another embodiment of the present invention, the base wall width may be sized and configured to store a minimum laser fiber wind length of at least 20 feet.

BRIEF DESCRIPTION OF THE DRAWINGS

These and other features and advantages of the various embodiments disclosed herein will be better understood with respect to the following description and drawings, in which like numbers refer to like part throughout, and in which.

DETAILED DESCRIPTION

The drawings referred to herein are for the purposes of illustrating the preferred embodiment of the present invention and not for the purposes of limiting the same.

Figure 1:
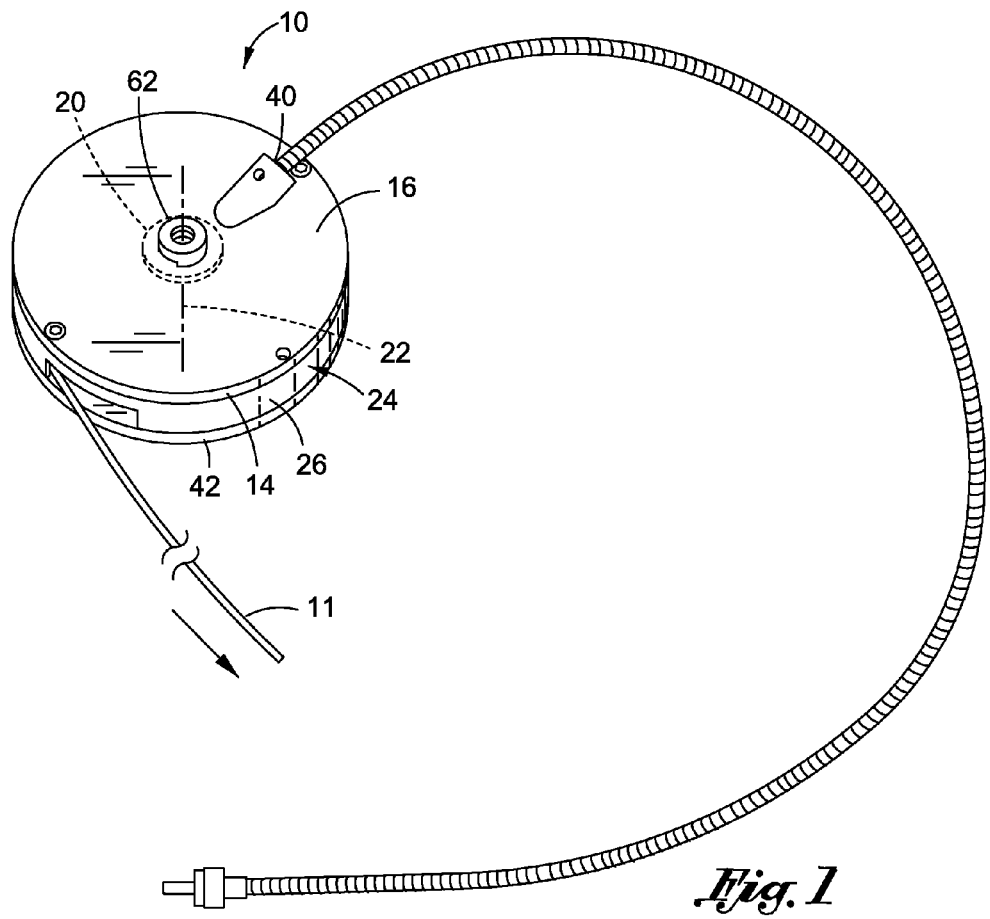
FIG. 1 is a perspective view of an embodiment of the laser fiber reel having a cylindrical wheel, base and laser fiber input port on the base plate.
Figure 2:
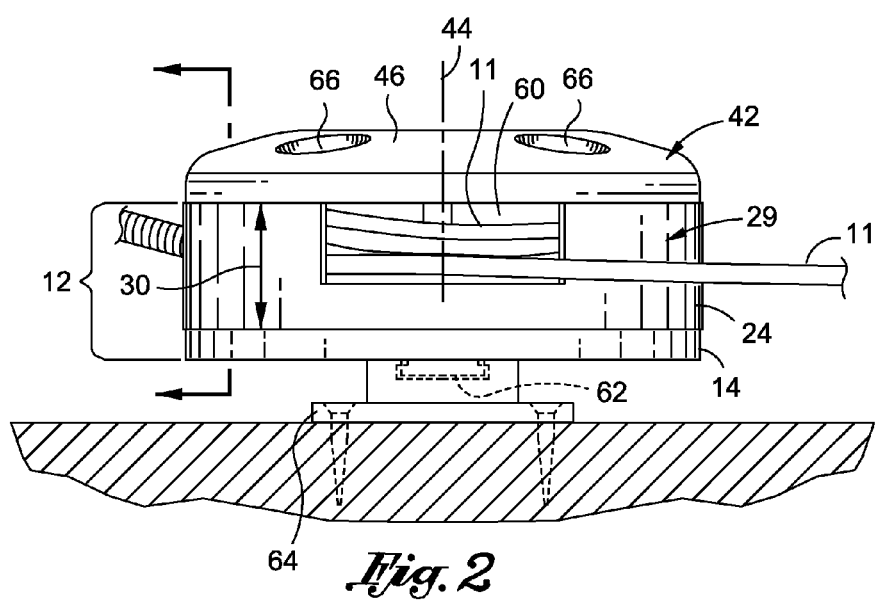
FIG. 2 is a side view of an embodiment of the laser fiber reel depicting a plurality of grip channels on the cylindrical wheel, a mounting post on the base plate mounted to a mounting clip, and the extension of the laser fiber though a laser fiber output aperture.

FIGS. 1 and 2 are perspective and cross-sectional views of various embodiments of the optical laser fiber reel 10. In these figures, the base 12 is shown to have a base plate 14 with a base plate outer surface 16. The base plate 14 further has a base hub 20 defining a base hub axis 22 orthogonal to the base plate 14. The base further has a base wall 24 generally orthogonal to the base plate 14 and concentric to the base hub 20. The base wall 24 further has a base wall outer surface 26 and a base wall inner surface 28. The base plate outer surface 16 also has a laser fiber input port 40 operative to receive optical laser fiber 11 into the fiber reel 10. As shown in FIG. 1, the laser fiber 11 may be readily extended from or retracted back into the fiber reel 10 through the laser fiber input port 40.

FIG. 2 is an embodiment of the fiber reel 10 having a cylindrical wheel 42 defining a wheel axis 44 concentric to the base hub 20. The wheel 42 is shown to have a wheel outer surface 46 and a plurality of grip channels 66 disposed on the wheel outer surface 46. The wheel 42 is rotateably engaged with the base 12. In the embodiment in FIG. 2, the fiber reel 10 also has a mounting post 62 on the base plate outer surface 16 mountable to a mounting clip 64. This feature uniquely enables the fiber reel 10 to be mounted to a variety of different objects or surfaces, including but no limited to the laser system from which it transmits laser energy as well as in other locations conveniently accessible to the target site at which the surgical or dental procedure is being performed. The mounting post 62 may be readily removed from the mounting clip 64, thereby enabling the convenient sterilization of the fiber reel 10 in an autoclave or use at a different location. The mounting clip 64 also fixes the mounting post 62 in a stable position, thereby preventing the base plate from moving. Still referring to FIG. 2, the base wall 24 is shown to have a base wall width 30 that is not less than a minimum laser fiber wind length 32. As used herein, the term "minimum laser fiber wind length" 32 should not be construed narrowly, but rather broadly to mean the total pre-cut length of the optical laser fiber 11 that may be wound into the fiber reel 10 without stacking on top of itself. This feature may uniquely enable a predetermined length of laser fiber 10 to be wound into the fiber reel without being bent or otherwise damaged. Clearly, this is a desirable feature of the laser fiber reel 10, as any damage to the fiber reel 11 could impair or even cause failure of the transmission of laser energy from a laser device through the fiber 11. For example, the minimum laser fiber wind length may be approximately twenty feet. However, it is also contemplated within the scope of the present invention that the various aspects of the laser fiber reel 10, including the fiber cage width 38 discussed below and the base wall width 30, may be sized and configured to store a minimum laser fiber wind length 32 of various sizes less than or greater than twenty feet.

FIGS. 3-4, 6-7 depict a fiber cage 34 proximate to the base wall inner surface 28 and concentric to the base hub 20. The fiber cage 34 is operative to store the laser fiber 11 by enabling the laser fiber 11 to be radially wound into the reel 10. The fiber cage 34 has a fiber cage radius 35 measured from the base hub 20 that is greater than or equal to a minimum laser fiber bend radius 36. As used herein, the term "minimum laser fiber bend radius" should not be construed narrowly, but rather broadly to mean the minimum radius at which the laser fiber 11 may be bent without being deformed or damaged. That is, the "minimum laser fiber bend radius" is the radius below which the laser fiber should not be bent. Micro-bending of the laser fiber 11 may cause light attenuation induced by deformation. Macro-bending may cause the leakage of light through the fiber cladding due to excessive bending. In the embodiment depicted in FIGS. 3 and 4, the fiber cage radius is sized and configured to be no greater than the minimum laser fiber bend radius 36 for a laser fiber 11 between 200 and 400 micrometers. For example, the minimum laser fiber bend radius 36 for a laser fiber 11 of 200 micrometers is approximately 2 cm., while the laser fiber bend radius for a laser fiber 11 of 400 micrometers is approximately 4 cm. However, it is also contemplated within the scope of the present invention that the various aspects of the fiber reel 10 may be employed with a fiber cage 34 having a fiber cage radius 35 that is no less than the minimum laser fiber bend radius 36 of a laser fiber 11 of various sizes less than 200 micrometers or greater than 400 micrometers.

The laser fiber reel 10 is innovative in that it uniquely enables laser fibers 11 of varying sizes to be uniformly housed, such that they are not bent below their minimum laser fiber bend radius 36. This may prevent possible damage caused by breakage of the laser fiber 11 after having been bent below the minimum laser fiber bend radius 36. As discussed above, such bending or breakage could cause the laser energy from the laser source to become attenuated due to deformation. The light of the laser energy may also leak out of a laser fiber 11 that has been cracked or otherwise damaged due to excessive bending. The laser fiber reel 10 is further innovative in that the fiber cage width 38 enables the laser fiber 11 to be wound around the fiber cage 34, such that the laser fiber 11 does not wind around itself. This feature may further mitigate the likelihood of possible damage to or breakage of the laser fiber 11 due to excessive coiling, "bunching", or "backup" in the fiber reel 10. The compact configuration of the fiber reel 10 enables it to be rarely stored or transported from one procedure site to the next. As discussed further below, the fiber reel 10 is further innovative in that the laser fiber 11 may continue to be housed in the fiber reel 10 during the process of sterilization.

Figure 3:
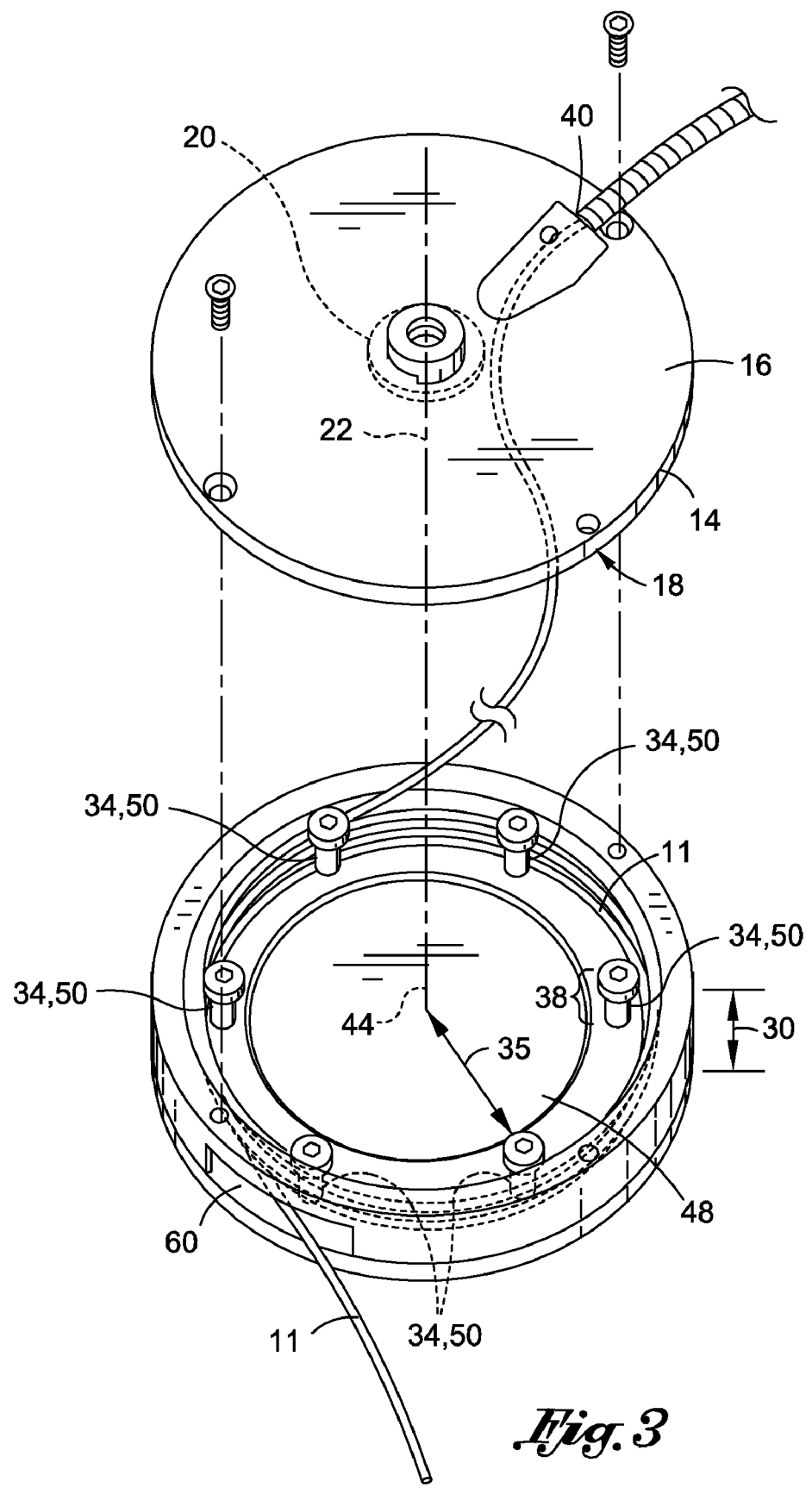
FIG. 3 is a perspective view of an embodiment of the laser fiber reel having a fiber cage comprising six evenly spaced wheel posts proximate to the base wall inner surface and concentric to the base hub, with the wheel post being rotateably engageable with a spacer disposed on the base wall inner surface.
Figures 4, 5:
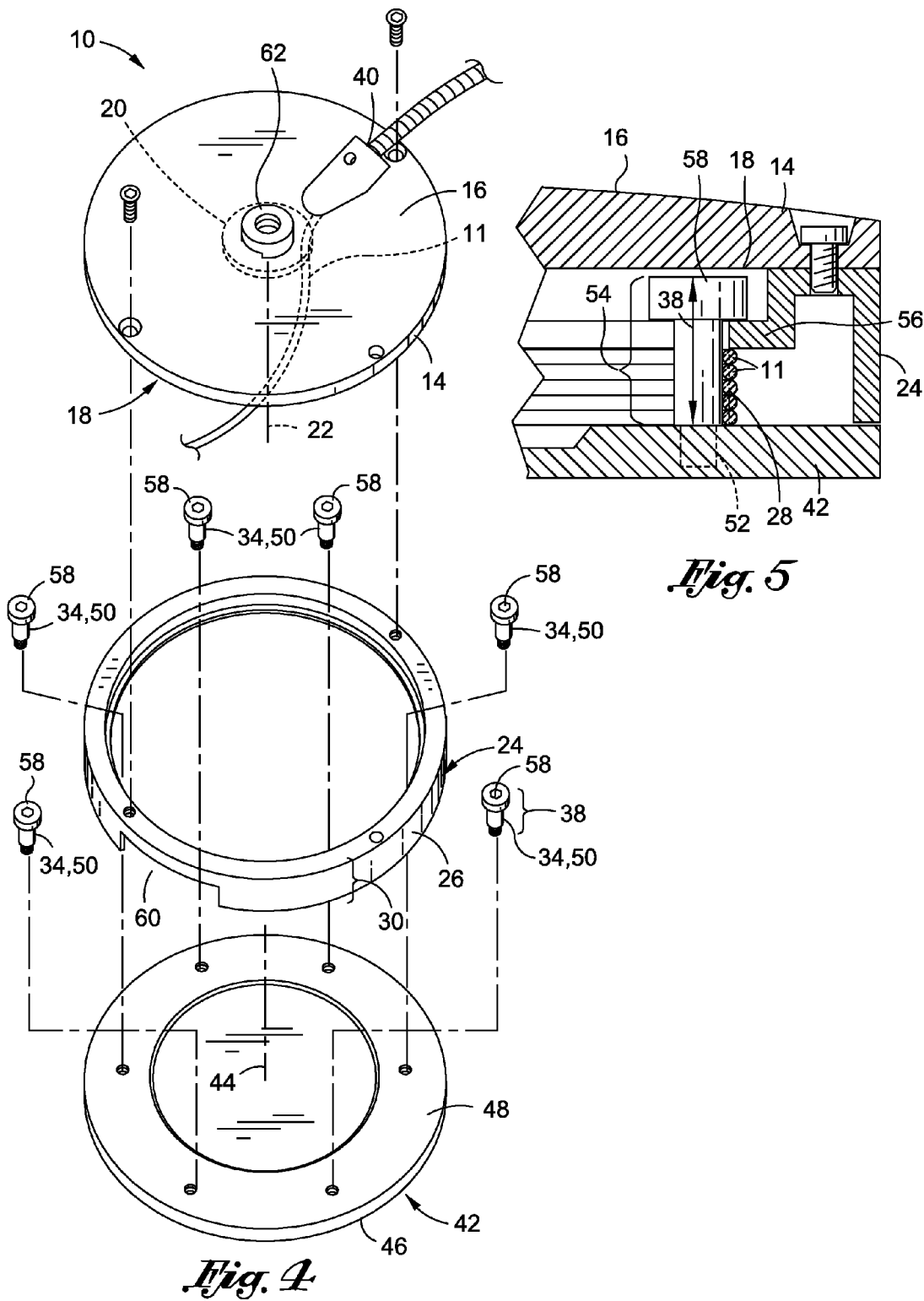
FIG. 4 is a perspective view of an embodiment of the laser fiber reel having a fiber cage comprising six evenly spaced wheel posts proximate to the base wall inner surface and concentric to the base hub, with the wheel post being rotateably engageable with a spacer disposed on the base wall inner surface.
FIG. 5 is a cross-sectional view of an embodiment of the fiber reel depicting a wheel post mounted to the wheel inner surface and extending toward the base plate inner surface, with a rounded spacer knob on the wheel post engageable with a spacer disposed on the base wall inner surface.

In the embodiment depicted in FIGS. 3 and 4, the fiber cage 34 is a plurality of six evenly spaced wheel posts 50. Each wheel post 50 has a wheel post first end 52 mounted to the wheel inner surface 48 and a wheel post second end 54 extending from the wheel inner surface 48 toward the base plate inner surface 18, proximate to the base wall inner surface 28. In this embodiment, each wheel post second end 54 is rotateably engageable with a spacer 56 disposed on the base wall inner surface 28. The wheel 42 has an opposing wheel inner surface 48 facing the base plate inner surface 18 as shown in FIG. 4. In this embodiment, each wheel post second end 54 has a generally rounded spacer knob 58 sized and configured to be rotateably disposable beneath the spacer 56. As shown in the embodiment in FIG. 5, each wheel post 50 is mounted to the wheel inner surface 48 and extends toward the base plate inner surface 18 proximate to the base wall inner surface 28. Each wheel post second end 54 is rotateably engageable with the spacer 56 mounted to the base wall inner surface 28. The spacer knob 58 on the wheel post second end 54 is rotateably disposable beneath the spacer 56.

Figure 6:
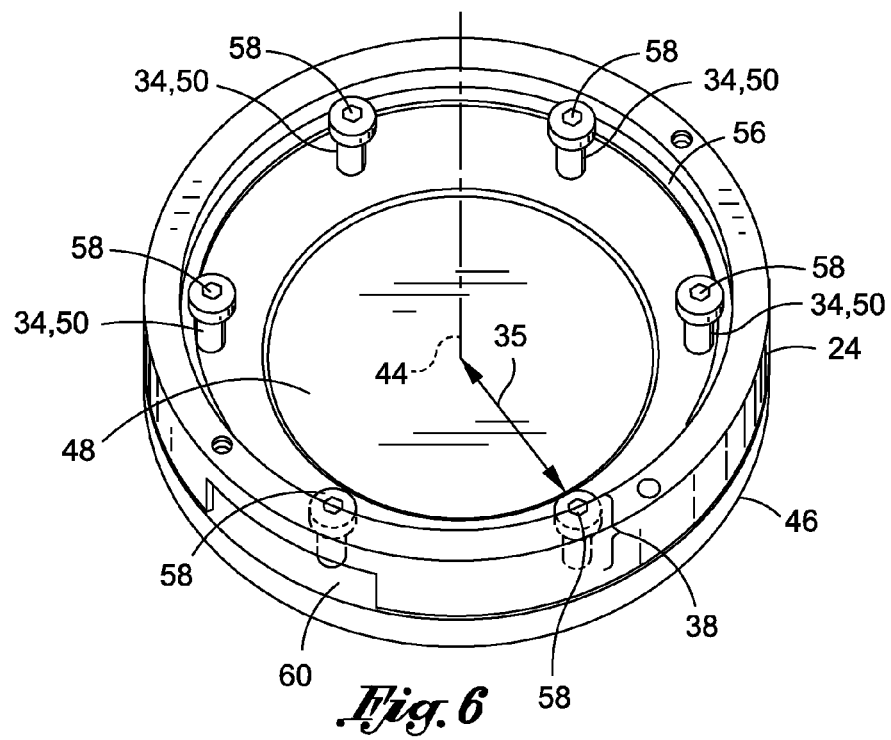
FIG. 6 is a perspective view of an embodiment of the fiber reel showing the fiber cage radius as measured from the base hub.
Figure 7:
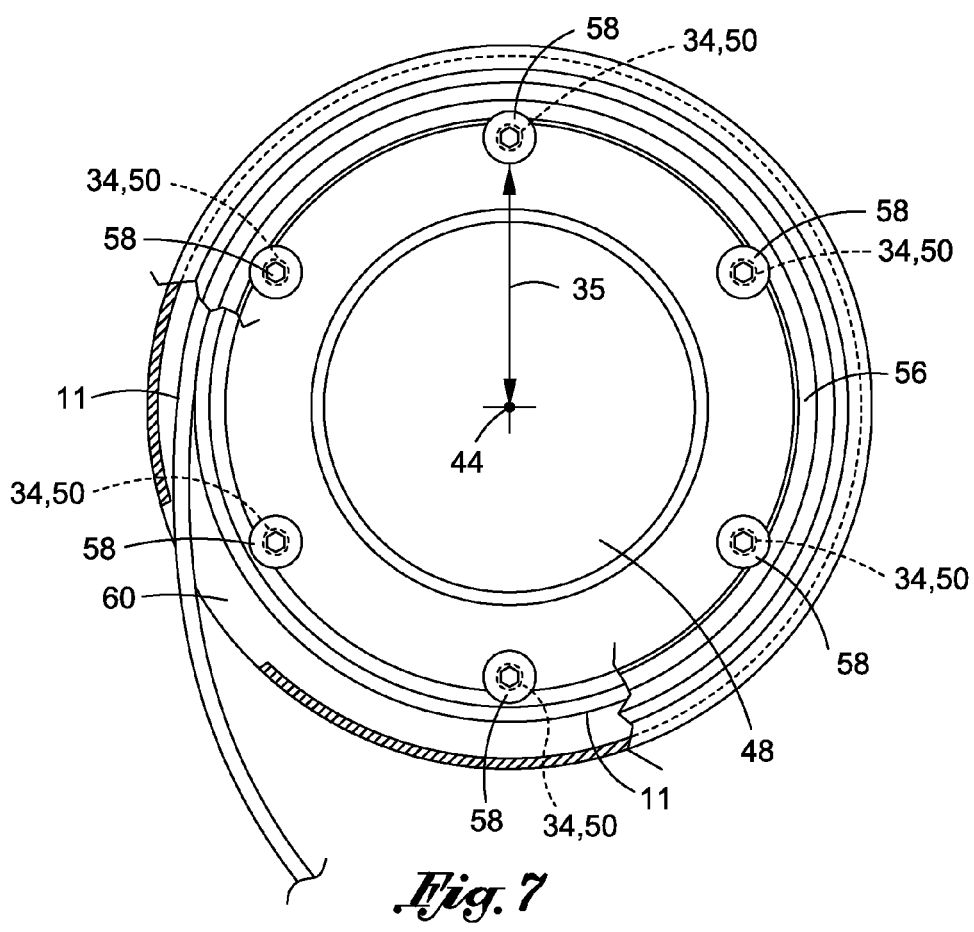
FIG. 7 is a top view of an embodiment of the fiber reel showing the extension of the fiber reel through the laser fiber output aperture on the base wall.

As discussed above, the wheel post second end 54 has a fiber cage width 38 that is not less than the minimum laser fiber wind length 32 of the laser fiber 11. As shown in FIGS. 3, 4, and 6, this configuration of the fiber reel 10 uniquely enables the cylindrical wheel 42 to be rotateably engageable with the base 12, thereby enabling the efficient extension and retraction of the fiber reel 11 through the laser fiber output aperture 60 by turning the wheel 42. For example, depending on the direction in which the laser fiber 11 is wound on the wheel post 50, the turning of the wheel 42 in a counterclockwise direction may release the laser fiber 11 out of the reel 10. Likewise, the turning of the wheel 42 in a clockwise direction may retract the laser fiber into the reel 10.

Figure 8:
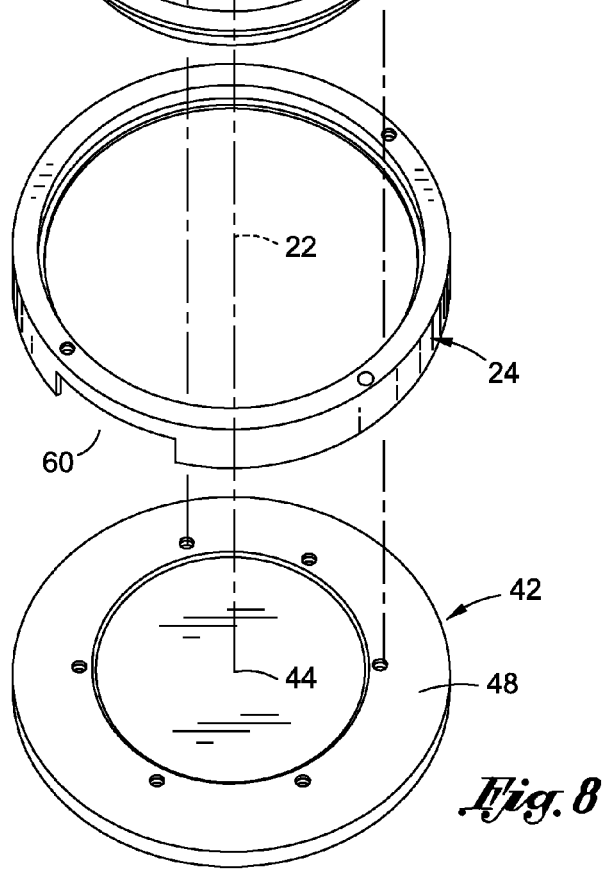
FIG. 8 is a cross-sectional view of an embodiment of the fiber reel having a spool for a fiber cage mounted to the wheel inner surface.

Referring now to the embodiment of the fiber reel 10 in FIG. 8, the fiber cage 34 may be a generally round spool 70. In an embodiment of the fiber reel 10 without a wheel 42, the spool 70 may be mountable to the base plate inner surface 18. In an embodiment of the fiber reel 10 with a wheel 42, the spool 70 may be mountable to the wheel inner surface 48. However, in both embodiments, the spool 70 has a fiber cage radius 35 as measured from the base hub 20 that is greater than or equal to the minimum laser fiber bend radius 36 of the laser fiber 11. Also, in both of these embodiments, the spool 70 has a fiber cage width 38 not less than the minimum laser fiber wind length 32 of the laser fiber 11.

Figure 9:
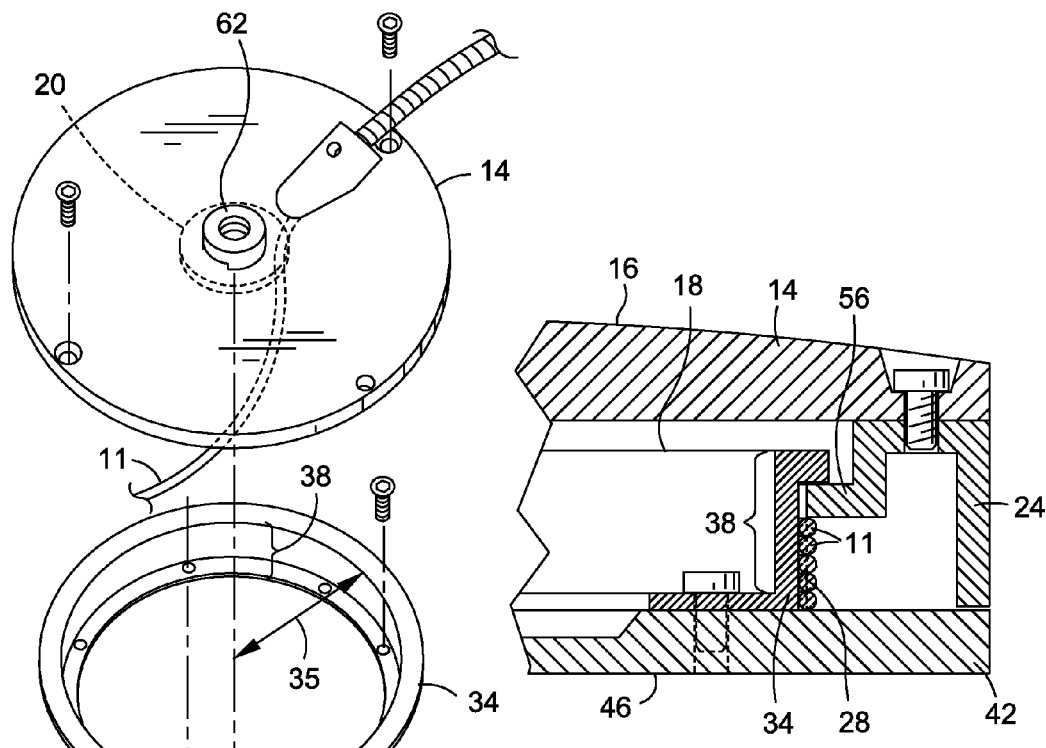
FIG. 9 is a perspective view of an embodiment of the fiber reel having a spool for the fiber cage mounted onto the wheel inner surface.

Referring to FIG. 9, the spool 70 is shown mounted to the wheel inner surface 48. The spool 70 extends toward the base plate inner surface 18 proximate to the base wall inner surface 28. In this embodiment, the spool has a fiber cage lip 68 that is sized and configured to be rotateably disposable proximate the spacer 56.

In a preferred embodiment of the claimed invention, the fiber reel 10 is made of metal. However, it is contemplated within the scope of the present invention that the fiber reel 10 may be made of any material capable of withstanding very high temperatures to which it may be exposed during the sterilization of the laser fiber 11. This feature uniquely enables the laser fiber 11 to be placed for example in an autoclave while it is still wound on the fiber reel 10, thereby making the sterilization process and storing of the laser fiber 11 more efficient. It is foreseeable that the laser fiber 11 will be exposed to various pathogens during the medical and dental procedures for which it has been used. Typically, the end of the fiber 11 that is used at the surgical or dental site is cut off upon completion of the procedure and then sterilized in an autoclave. The laser fiber reel 10 enables the medical or dental technician to remove that portion of the laser fiber exposed to the target site, retract the remaining laser fiber 11 onto the fiber cage in the fiber reel 10, and then place the wound laser fiber reel into an autoclave for sterilization. This configuration obviates the need to remove the laser fiber from the laser fiber reel 10.

What is claimed is:

1. A universal laser fiber reel for use with an optical laser fiber, the reel comprising:

a generally circular base having a base plate, the base plate having a base plate outer surface and a base plate inner surface, the base plate further having a base hub defining a base hub axis, the base further having a generally circular base wall generally orthogonal to the base plate and concentric to the base hub, the base wall having a base wall outer surface and a base wall inner surface, the base wall inner surface having a spacer, the base wall further having a base wall width not less than a minimum laser fiber wind length;

a generally cylindrical wheel defining a wheel axis concentric to the base hub, the wheel having a wheel outer surface and an opposing wheel inner surface facing the base plate inner surface, the wheel being rotatably engageable with the base;

a fiber cage being a spool proximate the base wall inner surface and concentric to the base hub operative to radially store the laser fiber in the reel, the fiber cage having a fiber cage radius as measured from the base hub greater than or equal to a minimum laser fiber bend radius, the fiber cage having a fiber cage width not less than the minimum laser fiber wind length of the laser fiber, the fiber cage having a plurality of six evenly spaced wheel posts, each wheel post having a wheel post first end mounted to the wheel inner surface and a wheel post second end extending from the wheel inner surface toward the base plate inner surface proximate to the base wall inner surface, each wheel post second end having a generally rounded spacer knob sized and configured to be rotatably engageable with the spacer; and a laser fiber input port on the base plate outer surface operative to receive the laser fiber into the reel.

2. The laser fiber reel as claimed in claim 1 further includes a laser fiber output aperture on the base wall operative to enable the release or retraction of the laser fiber.

3. The laser fiber reel as claimed in claim 1 is made of metal.

4. The laser fiber reel as claimed in claim 1 further includes a mounting post on the base plate outer surface operative to mount the laser fiber reel to a mounting clip.

5. The laser fiber reel as claimed in claim 1 further includes a plurality of grip channels on the wheel outer surface.

6. The laser fiber reel as claimed in claim 1, wherein the fiber cage radius of the fiber cage is sized and configured for a laser fiber between 200 and 400 micrometers.

7. The laser fiber reel as claimed in claim 1, wherein the fiber cage radius of the fiber cage is sized and configured for a laser fiber greater than or equal to 400 micrometers.

8. The laser fiber reel as claimed in claim 1, wherein the fiber cage radius of the fiber cage is sized and configured for a laser fiber less than or equal to 200 micrometers.

9. The laser fiber reel as claimed in claim 1, wherein the base wall width is sized and configured to store a minimum laser fiber wind length of at least 20 feet.

10. The laser fiber reel as claimed in claim 1, wherein the fiber cage is mountable to the base plate.

11. The laser fiber reel as claimed in claim 1, wherein the fiber cage is mountable to the wheel.

* * * * *